United States Patent
Schmid et al.

(10) Patent No.: US 12,357,581 B2
(45) Date of Patent: Jul. 15, 2025

(54) NANOPARTICLES COMPRISING COPOLYMERIC OR HOMOPOLYMERIC COMPOUNDS WHICH COMPRISE CYANOACRYLATE SUBUNITS

(71) Applicant: SINTEF TTO AS, Trondheim (NO)

(72) Inventors: Ruth Schmid, Tiller (NO); Peter Molesworth, Leirfossvegen (NO); Yrr Mørch, Trondheim (NO)

(73) Assignee: SINTEFF TTO AS (NO)

( * ) Notice: Subject to any disclaimer, the term of this patent is extended or adjusted under 35 U.S.C. 154(b) by 773 days.

(21) Appl. No.: 17/602,344

(22) PCT Filed: Feb. 26, 2020

(86) PCT No.: PCT/EP2020/055066
§ 371 (c)(1),
(2) Date: Oct. 8, 2021

(87) PCT Pub. No.: WO2020/207655
PCT Pub. Date: Oct. 15, 2020

(65) Prior Publication Data
US 2022/0160645 A1    May 26, 2022

(30) Foreign Application Priority Data
Apr. 10, 2019  (NO) .................................. 20190491

(51) Int. Cl.
*A61K 31/337*  (2006.01)
*A61K 9/51*   (2006.01)

(52) U.S. Cl.
CPC .......... *A61K 9/5138* (2013.01); *A61K 31/337* (2013.01)

(58) Field of Classification Search
CPC ............................ A61K 9/5138; A61K 31/337
See application file for complete search history.

(56) References Cited

U.S. PATENT DOCUMENTS

| | | |
|---|---|---|
| 9,062,151 B1 | 6/2015 | Kim |
| 2002/0034474 A1 | 3/2002 | Sabel et al. |
| 2005/0287216 A1* | 12/2005 | Loomis ............... B82Y 5/00 424/486 |
| 2007/0245500 A1 | 10/2007 | Brun et al. |
| 2008/0138418 A1 | 6/2008 | Lee et al. |
| 2008/0182776 A1 | 7/2008 | Lee et al. |
| 2009/0297613 A1 | 12/2009 | Ringe et al. |
| 2010/0015165 A1 | 1/2010 | Landfester et al. |
| 2011/0151243 A1 | 6/2011 | McArdle et al. |
| 2014/0238603 A1 | 8/2014 | Heemann et al. |
| 2015/0290357 A1 | 10/2015 | Chu |
| 2018/0325833 A1 | 11/2018 | Curic et al. |
| 2018/0343860 A1 | 12/2018 | Shirotake |

FOREIGN PATENT DOCUMENTS

| | | |
|---|---|---|
| EP | 0 470 722 A1 | 2/1992 |
| FR | 2 891 742 A1 | 4/2007 |
| FR | 2 899 801 A1 | 10/2007 |
| WO | 2012/131018 A1 | 10/2012 |
| WO | 2014/191502 A1 | 12/2014 |
| WO | 2016/121829 A1 | 8/2016 |
| WO | 2017/085212 A2 | 5/2017 |

OTHER PUBLICATIONS

McMahon et al. (2000).*
Pinedo et al. (2000).*
New progress in Obstetrics and Gynecology, edited by Li Xingmei et al, China Science and Technology Press, p. 471, Jun. 2008.
Biopharameutical Analysis, edited by Zhang Yixuan, China Medical Science Press, p. 267, Dec. 2015.
Nicolas and Couvreur, Rev. Nanomed. Nanobiotechnol., 2009, 1, 111-127.
Storm et al., Adv Drug Deliv Rev 1995, 17: 31-48.
Stolnik, Illum & Davis, Adv Drug Deliv Rev 1995, 16: 195-214.
Chauvierre, C., et al. (2003) Macromolecules 36(16): 6018-6027.
Lemarchand, C., et al. (2004). 58(2): 327-341.
Landfester, Macromol. Rapid Comm. 2001, 22, 896-936.
Landfester et al, Macromolecules 1999, 32, 5222-5228.
Ugelstad et al. (1973), J Polym Sci Polym Lett Ed 11:503-513.
Vauthier, C., J Drug Target. 2019 27(5-6) p. 502-524.
Kumari et al., Colloids Surf B Biointerfaces Biointerfaces. Jan. 1, 2010; 75(1):1-18.
Torchilin VP Nat Rev Drug Discov. Nov. 2014; 13(11):813-27.
Sulheim et al., J Nanobiotechnology. Jan. 8, 2016; 14():1.
Baier et al (Macromolecules 2012, 45, 3419-3427).
Tekle et al, Nano Lett. Jul. 2008; 8(7):1858-65.
Sulheim et al., Int J Mol Sci. Nov. 2017; 18(11): 2454.
Int. J. Pharm. 1992;84:13-22. doi: 10.1016/0378-5173(92)90210-S.
Robello et al, J. Polym Sci .: Part A: Pol. Chem. 37, 4570-4581 (1999).
Soppimath et al., Polymer News, 2000, vol. 25, No. 4, p. 141-142.
Norwegian Search Report issued Jul. 17, 2019 in related Norwegian Application No. 20190491, 2 pages.
International Search Report mailed Aug. 6, 2020 in related International Application No. PCT/EP2020/055066, 7 pages.

* cited by examiner

*Primary Examiner* — Paul V Ward
(74) *Attorney, Agent, or Firm* — Fox Rothschild LLP

(57) ABSTRACT

The invention relates to a nanoparticle comprising copolymeric or homopolymeric compounds which comprise cyanoacrylate subunits according to formula 2A, wherein each $R^1$ is independently selected from the group consisting of 2-ethylhexyl, 2-phenylethyl, neopentyl, 1-pentyl, 2-pentyl, 3-pentyl, 3,3-dimethyl-1-butyl, 3-methylbutyl, -heptyl, 2-heptyl, and 3-heptyl; and wherein the nanoparticle further comprises an active agent. The invention also provides compositions comprising the nanoparticles, and the nanoparticles for use in therapy or diagnosis, such as in the treatment of cancer or an infection, or for use in diagnostic imaging.

20 Claims, No Drawings

NANOPARTICLES COMPRISING COPOLYMERIC OR HOMOPOLYMERIC COMPOUNDS WHICH COMPRISE CYANOACRYLATE SUBUNITS

This application is a U.S. National Stage Application based on International Application No. PCT/EP2020/055066 filed Feb. 26, 2020, which claims priority from application No. 20190491 filed on Apr. 10, 2019 in Norway. The entire contents of these applications are incorporated herein by reference in their entireties.

FIELD OF THE INVENTION

The invention relates to nanoparticles comprising copolymeric or homopolymeric compounds which are formed from cyanoacrylate monomers. An active agent is encapsulated within in the nanoparticles. The invention also relates to compositions comprising the nanoparticles and their use in medicine, such as drug delivery and molecular imaging, agriculture, aquaculture, nutraceuticals, food/feed applications, cosmetics, self-healing, household applications and body care.

BACKGROUND OF THE INVENTION

The use of nanoencapsulation offers exciting possibilities in many markets, where volatile, sensitive, or harmful materials/compounds need to be protected/hidden/masked/separated and delivered/co-delivered to a desired target. This is of particular importance in the rapidly developing field of nanomedicine.

Two areas in which the use of nanoparticles has begun to demonstrate particular value are drug delivery and molecular imaging. However, in addition to medicinal applications, nanoparticles may also be highly advantageous in nanoencapsulation of various materials/compounds, such as aroma compounds, fragrances, flavours, dyes, nutraceuticals, herbicides and pesticides.

Nanoparticles for the delivery of therapeutic agents have the potential to circumvent many challenges associated with traditional delivery approaches, including lack of patient compliance to prescribed therapy, adverse side effects and poor clinical efficacy due to lack of targeted delivery and suboptimal biodistribution. Important technological advantages of nanoparticles for drug delivery include the ability to deliver water-insoluble and unstable drugs, incorporation of both hydrophobic and hydrophilic therapeutic agents and the ability to utilise various routes of administration. Nanoparticle delivery systems may also facilitate targeted drug delivery and controlled release applications, enhancing drug bioavailability at the site of action, reducing dosing frequency and overall dosage size, thereby minimising side effects. As a result of these potential advantages, a variety of nanoparticulate systems have been investigated for use as drug delivery vehicles. These include polymeric micelles, polymers, polymeric particles, liposomes, low-density lipoproteins, solid-lipid nanoparticles, dendrimers, hydrophilic drug-polymer complexes and ceramic nanoparticles.

Nanoparticle-based imaging agents may have increased circulation time and altered water-solubility, thereby avoiding rapid clearance. Many of the particulate imaging systems used to date are designed exclusively for blood pool and lymphatic system imaging. The use of targeting imaging systems has the potential to increase accumulation at the target site, leading to a higher sensitivity and thus enabling molecular imaging outside the blood pool and lymphatic system. It is envisaged that targeted nanoparticles which contain both therapeutic and imaging agents could enable the use of a single vehicle for diagnosis, treatment and follow-up monitoring of a disease.

Polymeric nanoparticles have received a great deal of attention in the field of medicine, in particular those comprising biodegradable polymers such as poly(lactic acid), poly(glycolic acid) and poly(alkyl cyanoacrylate), however those developed to date have limited effectiveness because of high clearance rates and their propensity to distribute through the whole body, including into healthy tissue.

Controlled delivery of an active agent using nanoparticles therefore remains a challenge and there is a need for the development of biocompatible compositions capable of extended delivery of active agents which provide prolonged circulation time and increased stability compared to administration of the active agent alone.

Long circulating nanoparticles, i.e. those with enhanced stability in the circulatory system, have been investigated and contribute to addressing these issues. These types of nanoparticles have a hydrophilic shell around the nanoparticles, known as a stealth corona. Stealth-structured nanoparticles are well known and have been prepared with a variety of nanoparticle cores and with a range of polymeric shells, as discussed in Nicolas and Couvreur in *Rev. Nanomed. Nanobiotechnol.*, 2009, 1, 111-127, Storm et al., *Adv Drug Deliv Rev* 1995, 17: 31-48 and Stolnik, Ilium & Davis, *Adv Drug Deliv Rev* 1995, 16: 195-214. Their use in the encapsulation of therapeutic agents has also been described in, for example, US 2002/0034474. A commercially available example is Doxil®, which comprises pegylated liposomes containing doxorubicin.

Many methods for preparing nanoparticles are known, such as emulsion polymerisation, self-assembly and nanoprecipitation. Anionic emulsion polymerisation is described in, for example, US 2008/0138418 and radical polymerisation described in Chauvierre, C., et al. (2003) *Macromolecules* 36(16): 6018-6027 and Lemarchand, C., et al. (2004). 58(2): 327-341.

Miniemulsion processes are known for the production of nanoparticles with average sizes typically in the range 1-1000 nm, most typically 50-500 nm as disclosed e.g. in Landfester in *Macromol. Rapid Comm.* 2001, 22, 896-936 and Landfester et al in *Macromolecules* 1999, 32, 5222-5228. The method was first described by Ugelstad et al. (1973) *Emulsion polymerization: initiation of polymerization in monomer droplets. J Polym Sci Polym Lett Ed* 11:503-513.

Nanoparticles of poly(alkyl cyanoacrylate), PACA NP, are known in the art (Vauthier, C., *J Drug Target.* 2019 27(5-6) p 502-524).

In US 2008/182776 and US 2010/015165 miniemulsion polymerisation processes for the preparation of poly(alkyl cyanoacrylate) nanoparticles are described. An advantageous process for preparing poly(alkyl cyanoacrylate) nanoparticles is also described in WO 2014/191502.

Poly(alkyl cyanoacrylate) (PACA), first developed and approved as a surgical glue, was later proven to be a promising drug carrier due to its high loading capacity and biodegradability, and is currently being used in multiple late-stage clinical trials (Kumari A, Yadav S K, Yadav S C, *Colloids Surf B Biointerfaces.* 2010 Jan. 1; 75(1):1-18, Torchilin V P *Nat Rev Drug Discov.* 2014 November; 13(11):813-27). PACA nanoparticles fulfill basic requirements for use as medical or pharmaceutical products as they are biodegradable, and their degradation rate in cell culture, ranging from a few hours to several days, can be controlled by the choice of production method and the monomer used (Sulheim E, Baghirov H, von Haartman E, Bøe A, Åslund A K, Mørch Y, Davies C de L, *J Nanobiotechnology*. 2016 Jan. 8; 14( ):1.).

PACA nanoparticles are made from polymerizable cyanoacrylate monomers. Cyanoacrylates are known in the art as strong fast-acting adhesives with many applications, both in industrial, medical, and household uses. As cyanoacrylates are mainly used as adhesives, the cyanoacrylate availability is dominated by glue manufacturers. Thus, the most commonly used monomer for production of nanoparticles to be used in medicine are 1-butyl, 2-ethyl-butyl, 1-octyl and isohexyl cyanoacrylate. Another previously known monomer is propargyl cyanoacrylate (PPCA). It has been demonstrated in Baler et al (*Macromolecules* 2012, 45, 3419-3427) that nanoparticles made of a combination of n-butyl and propargyl cyanoacrylates can be used with a copper based click reaction to functionalize such nanocapsules.

There is a rising awareness regarding toxicity of drugs, additives and additional compounds used in medical delivery systems, in particular as nanotoxicology has become a large research field. Evaluating nanoparticle (NP) toxicity is challenging because the toxic effects can originate from both intact nanoparticles and their degradation products. For intact and partly degraded nanoparticles the size, shape, surface charge, surface molecules and core materials can all be the source of toxic effects. Furthermore, the route of cellular entry and intracellular accumulation of the nanoparticles is also expected to be important (Tekle C, Deurs By, Sandvig K, Iversen T G *Nano Lett*. 2008 July; 8(7):1858-65). As seemingly small changes in NP chemistry can cause dramatic differences in potency and safety, it is important to characterize NP interactions in biological systems.

In addition, most polymeric nanoparticles have limited loading capacity, often lower than liposomes. Thus, a greater number of particles often need to be used in order to achieve a sufficient dosage of active agent at the disease site. In view of this, the toxicity profile of the polymers is of importance and low toxicity is assessed in order to achieve a good risk/benefit ratio. Thus, both low toxicity and improved loading capacity are desired features in polymeric nanoparticles.

Cytotoxicity of known PACA NP has been investigated in Sulheim et al, *Int J Mol Sci*. 2017 November; 18(11): 2454). It is previously known that the monomer has a significant impact on the toxicity of otherwise similar nanoparticles (*Int. J. Pharm*. 1992; 84:13-22. doi: 10.1016/0378-5173(92) 90210-S). In Sulheim et al, 2017, it was concluded that understanding the toxicity of nanoparticles is challenging, and that no single property can explain the observed toxic effects of PACA nanoparticles.

The aim of the present invention is to provide new and improved nanoparticles and their use in medicine. It is a particular aim to provide new nanoparticles of low toxicity. If in addition the particles demonstrate an improved loading capacity or if loading of an improved range of compounds is possible, this is particularly interesting.

SUMMARY OF THE INVENTION

The invention relates to nanoparticles which are prepared from cyanoacrylate monomers selected from the group consisting of 2-ethylhexyl (2-EHCA), 2-phenyl ethyl (2-PECA), neopentyl (NPCA), 1-pentyl (1-PCA), 2-pentyl (2-PCA), 3-pentyl (3-PCA), 3,3-dimethyl-1 butyl (3,3-DMBCA), 1-heptyl (1-HPCA), 2-heptyl (2-HPCA), 3-heptyl (3-HPCA) or 3-methylbutyl (3-MBCA) cyanoacrylates.

In one aspect, the present invention provides a nanoparticle comprising copolymeric or homopolymeric compounds which comprise cyanoacrylate subunits according to formula 2A:

(2A)

wherein each $R^1$ is independently selected from the group consisting of 2-ethylhexyl, 2-phenyl-ethyl, neopentyl, 1-pentyl, 2-pentyl, 3-pentyl, 3,3-dimethyl-1-butyl, 3-methylbutyl, 1-heptyl, 2-heptyl, and 3-heptyl; and wherein the nanoparticle further comprises an active agent.

The nanoparticle may be made from the anionic or radical polymerization of a miniemulsion.

The nanoparticle may be made from the anionic polymerization of a miniemulsion comprising 3-methylbutyl cyanoacrylate.

The nanoparticle comprises an active agent. The active agent may be a medical component, such as an active pharmaceutical ingredient (API), i.e. a therapeutic agent or a diagnostic agent. The active agent is preferably encapsulated within the nanoparticle.

The active agent may be selected from the group consisting of alpelisib, a taxane, such as cabazitaxel (CBZ) and docetaxel, a platin, such as oxaliplatin, mupirocin, belinostat, Nile red or NR668.

The nanoparticle may comprise copolymeric compounds made from the anionic polymerization of a miniemulsion comprising the polymerizable cyanoacrylate monomers and the active agent.

In one embodiment the active agent is cabazitaxel.
In one embodiment the active agent is alpelisib.
In one embodiment the active agent is oxaliplatin.

The present invention also provides a method of forming the nanoparticle of the invention, the method comprising the anionic or radical polymerization of an oil-in-water miniemulsion, wherein said miniemulsion comprises:

(i) cyanoacrylate monomers according to formula 2

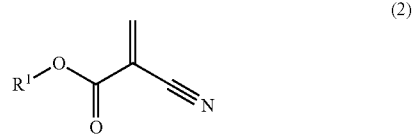

(2)

wherein each $R^1$ is independently selected from the group consisting of 2-ethylhexyl, 2-phenyl-ethyl, neopentyl, 1-pentyl, 2-pentyl, 3-pentyl, 3,3-dimethyl-1-butyl, 3-methylbutyl, 1-heptyl, 2-heptyl, and 3-heptyl;

(ii) at least one surfactant;
(iii) one or more active agents;
(iv) optionally an anionic polymerisation initiator or a radial polymerisation initiator; and
(v) optionally an anionic and/or radical inhibitor.

The present invention also provides a composition comprising one or more nanoparticles as defined herein, and optionally one or more pharmaceutically acceptable carriers, diluents or excipients.

The present invention also provides the nanoparticles as defined herein, or a composition containing said nanoparticles, for use in therapy or diagnosis.

The present invention also provides the nanoparticles as defined herein, or a composition containing said nanoparticles, for use in drug delivery.

The present invention also provides the nanoparticles as defined herein, or a composition containing said nanoparticles, for use in the treatment of cancer.

The present invention also provides the nanoparticles as defined herein, or a composition containing said nanoparticles, for use in the treatment of infections of the human or animal body.

The present invention also provides the nanoparticles as defined herein, or a composition containing said nanoparticles, for use in diagnostic imaging (of the human or animal body).

The present invention also provides a method for the treatment of cancer, the method comprising administering (an effective amount of) the nanoparticles as defined herein, or a composition containing said nanoparticles, to a subject in need thereof, preferably a human.

The present invention also provides a method for the treatment of an infection, the method comprising administering (an effective amount of) the nanoparticles as defined herein, or a composition containing said nanoparticles, to a subject in need thereof, preferably a human.

The present invention also provides the use of the nanoparticles as defined herein in molecular imaging (of the human or animal body), agriculture, aquaculture, ex-vivo antibacterial applications, nutraceuticals, food/feed applications, cosmetics, self-healing, household applications or body care, preferably molecular imaging.

The present invention is defined by the attached claims. Further optional features of the present invention and definition of terms are disclosed in the detailed description below.

Definitions

As used herein, the abbreviation "ACA" include both alkyl cyanoacrylate and aryl substituted alkyl cyanoacrylates, i.e. an alkyl cyanoacrylate that further comprises an aryl side group.

As used herein, the term "PACA" means poly(alkyl cyanoacrylate), i.e. a polymer formed from ACA monomers.

The polymerization of specific alkyl cyanoacrylate monomers will result in specific polymers. Thus, polymerizing butyl cyanoacrylate (BCA) monomers will result in poly (butyl cyanoacrylate), herein termed "PBCA".

As used herein, the term "POCA" means poly(octyl cyanoacrylate), which is a polymer formed from octyl cyanoacrylate (OCA) monomers.

As used herein, the term "PEBCA" means poly(2-ethylbutyl cyanoacrylate), which is a polymer formed from 2-ethylbutyl cyanoacrylate (EBCA) monomers.

As used herein, the term "NP" means nanoparticle. As such, the term "PACA NPs" means poly(alkyl cyanoacrylate) nanoparticles. As used herein, the term "nanoparticle" means any particle having a largest dimension of less than 1000 nm, such as from 1 nm to 1000 nm. Preferably, the term "nanoparticle" means any particle having a largest dimension of from 30 to 500 nm.

The term "targeting moiety" is used herein to describe any molecule that can be bound to the surface of the nanoparticle and result in selective binding to specific cells or biological surfaces.

For clarity, the structures of 2-ethylhexyl, 2-phenyl-ethyl, neopentyl, 1-pentyl, 2-pentyl, 3-pentyl, 3,3-dimethyl-1-butyl, 3-methylbutyl, 1-heptyl, 2-heptyl, and 3-heptyl are set out below:

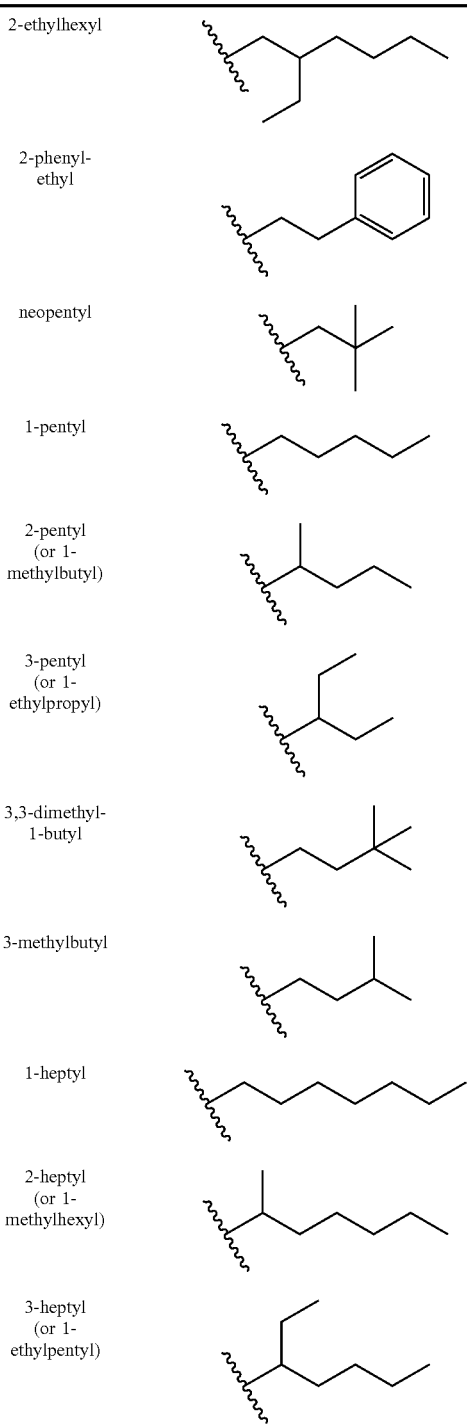

As used herein, the terms "2-EHCA", "2-PECA", "NPCA", "1-PCA", "2-PCA", "3-PCA", "3,3-DMBCA", "1-HPCA", "2-HPCA", "3-HPCA" and "3-MBCA" mean 2-ethylhexyl cyanoacrylate, 2-phenylethyl cyanoacrylate, neopentyl cyanoacrylate, 1-pentyl cyanoacrylate, 2-pentyl cyanoacrylate, 3-pentyl cyanoacrylate, 3,3-dimethyl-1 butyl cyanoacrylate, 1-heptyl cyanoacrylate, 2-heptyl cyanoacrylate, 3-heptyl cyanoacrylate and 3-methylbutyl cyanoacrylate respectively.

As used herein, the term "subunit" means a single unit that together with other subunits forms a polymer. That is, a polymer is composed of many repeating subunits. The term "subunit" is also sometimes termed "repeating unit", "monomer unit", "monomer residue" or "mers".

As used herein, the term "comprises" or "comprising" includes the term "consists of" or "consisting of". The invention is directed to a nanoparticle comprising copolymeric or homopolymeric compounds which comprise the subunits specified herein (such as the subunits of formula 2A or formula 2B). Because "comprise" has an open interpretation, other non-specified subunits may also be present in the copolymeric or homopolymeric compounds.

The invention also encompasses a nanoparticle comprising copolymeric or homopolymeric compounds which consist essentially of the subunits specified herein (such as the subunits of formula 2A or formula 2B). In this case, specific further subunits may be present in the copolymeric or homopolymeric compounds other than those specifically recited in the relevant embodiment (e.g. the subunits of formula 2A or formula 2B), namely those subunits not materially affecting the essential characteristics of the copolymeric or homopolymeric compounds.

The invention also encompasses a nanoparticle comprising copolymeric or homopolymeric compounds which consist of the subunits specified herein. In this case, no subunits may be present in the copolymeric or homopolymeric compounds other than those specifically recited in the relevant embodiment (e.g. the subunits of formula 2A or formula 2B).

DETAILED DESCRIPTION

The invention provides nanoparticles comprising a poly(cyanoacrylate) homopolymer or copolymer.

One way of making poly(cyanoacrylate) nanoparticles, PACA NPs, is to prepare them from cyanoacrylate monomers (ACA) by the following scheme:

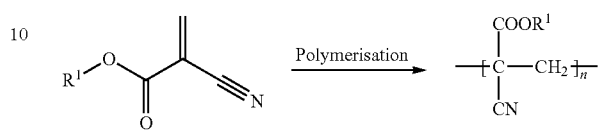

The cyanoacrylates used herein are various esters of cyanoacrylic acid. The acryl groups in the resin rapidly polymerize to form long chains with increasing molecular weight. In a biological system, the PACA nanoparticles degrade to alcohols and shorter, low-molecular weight water-soluble poly (cyano acrylic acid) fragments (D. R. Robello, T. D. Eldrigdge, M. T. Swanson, *J. Polym Sci.: Part A: Pol. Chem.* 37, 4570-4581 (1999). *Degradation and Stabilization of polycyanoacrylates*). This degradation is shown in the scheme below:

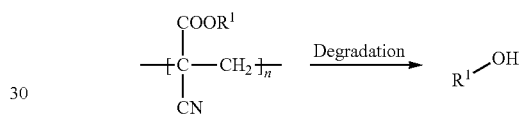

The cyanoacrylates and the controls used in the tests are listed in table 1, together with their abbreviations and their corresponding alcohols.

TABLE 1

Alcohols, cyanoacrylates, chemical structure and abbreviations.

| Alcohol name | Alcohol | Monomer | Cyanoacrylate |
|---|---|---|---|
| 2-ethylhexanol | ![structure] | 2-EHCA | ![structure] |
| 1-heptanol | ![structure] | 1-HPCA | ![structure] |
| 3-methylbutanol | ![structure] | 3-MBCA | ![structure] |
| 3-heptanol | ![structure] | 3-HPCA | ![structure] |

TABLE 1-continued

Alcohols, cyanoacrylates, chemical structure and abbreviations.

| Alcohol name | Alcohol | Monomer | Cyanoacrylate |
|---|---|---|---|
| Neopentanol | (CH₃)₃C-CH₂-OH | NPCA | neopentyl 2-cyanoacrylate |
| 2-phenylethanol | PhCH₂CH₂-OH | 2-PECA | 2-phenylethyl 2-cyanoacrylate |
| 1-pentanol | CH₃(CH₂)₄-OH | 1-PCA | pentyl 2-cyanoacrylate |
| 3-pentanol | (C₂H₅)₂CH-OH | 3-PCA | pent-3-yl 2-cyanoacrylate |
| 3,3-dimethyl-butanol | (CH₃)₃C-CH₂CH₂-OH | 3,3-DMBCA | 3,3-dimethylbutyl 2-cyanoacrylate |
| 2-heptanol | CH₃(CH₂)₄CH(OH)CH₃ | 2-HPCA | hept-2-yl 2-cyanoacrylate |
| 1-octanol (control) | CH₃(CH₂)₇-OH | 1-OCA | octyl 2-cyanoacrylate |
| 2-ethylbutanol (control) | (C₂H₅)₂CHCH₂-OH | 2-EBCA | 2-ethylbutyl 2-cyanoacrylate |
| 1-butanol (control) | CH₃(CH₂)₃-OH | 1-BCA | butyl 2-cyanoacrylate |

The present invention provides a nanoparticle comprising copolymeric or homopolymeric compounds which comprise cyanoacrylate subunits according to formula 2A:

$$\begin{array}{c} \text{COOR}^1 \\ | \\ -\!\!-\!\!\text{C}-\!\!\text{CH}_2\!\!-\!\!- \\ | \\ \text{CN} \end{array} \quad (2A)$$

wherein each $R^1$ is independently selected from the group consisting of 2-ethylhexyl, 2-phenyl-ethyl, neopentyl, 1-pentyl, 2-pentyl, 3-pentyl, 3,3-dimethyl-1-butyl, 3-methylbutyl, 1-heptyl, 2-heptyl, and 3-heptyl;

and wherein the nanoparticle further comprises an active agent.

The invention also provides a nanoparticle comprising copolymeric or homopolymeric compounds according to formula 1:

$$\begin{array}{c} \text{COOR}^2 \\ | \\ -\!\!\!+\!\!\text{C}-\!\!\text{CH}_2\!\!\frac{}{}_{n}\!- \\ | \\ \text{CN} \end{array} \quad (1)$$

wherein each $R^2$ is independently selected from a group having from 1 to 15 non-hydrogen atoms;

provided that at least one of the $R^2$ groups is an $R^1$ group, as defined above; and wherein the nanoparticle further comprises an active agent.

The integer 'n' may be any integer greater than 1. However, it is preferred that n is 5 or more, more preferably 10 or more. Preferably, n is 5000 or less, more preferably 3300 or less. A range of from 10 to 3300 is most preferred.

The molecular weight of the copolymeric or homopolymeric compounds of the invention is therefore preferably from 1000 to 1,000,000 g/mol, more preferably from 2000 to 700,000 g/mol.

The terminal groups of the copolymeric or homopolymeric compounds are generally —H and —OH, i.e. as shown below:

$$\begin{array}{c} \text{COOR}^2 \\ | \\ \text{H}-\!\!\!+\!\!\text{C}-\!\!\text{CH}_2\!\!\frac{}{}_{n}\!\text{OH} \\ | \\ \text{CN} \end{array}$$

Preferably, each of the non-hydrogen atoms are carbon atoms.

Each $R^2$ group may be linear or branched, and may include an aryl group.

Preferably, each $R^2$ is independently selected from a group having from 3 to 10 non-hydrogen atoms.

More preferably, each $R^2$ is independently selected from a group having from 5 to 8 non-hydrogen atoms.

Suitable $R^2$ groups include $C_{1-10}$ alkyl, $C_{1-10}$ alkenyl, $C_{1-10}$ alkynyl and $C_{1-8}$ alkyl-$C_{5-7}$ aryl.

Preferred $R^2$ groups include $C_{3-8}$ alkyl, $C_{3-8}$ alkenyl, $C_{3-8}$ alkynyl and $C_{1-5}$ alkyl-$C_{5-7}$ aryl.

More preferred $R^2$ groups include $C_{5-8}$ alkyl, $C_3$ alkynyl and $C_{1-3}$ alkyl-$C_6$ aryl.

Particularly suitable $R^2$ groups include all of those listed herein as suitable $R^1$ groups, as well as 1-octyl, 1-butyl, 2-ethylbutyl, 4-methylpentyl, 1-hexyl, ethyl and propargyl.

The polymers used in the present invention may be homopolymers or copolymers.

When the polymers are homopolymers, all of the cyanoacrylate subunits are the same. That is, the nanoparticle comprises homopolymeric compounds which consist of a single repeating cyanoacrylate subunit according to formula 2A.

Put another way, in this case the nanoparticle will comprise a compound according to formula 1A:

$$\begin{array}{c} \text{COOR}^1 \\ | \\ -\!\!\!+\!\!\text{C}-\!\!\text{CH}_2\!\!\frac{}{}_{n}\!- \\ | \\ \text{CN} \end{array} \quad (1A)$$

wherein $R^1$ is 2-ethylhexyl, 2-phenyl-ethyl, neopentyl, 1-pentyl, 2-pentyl, 3-pentyl, 3,3-dimethyl-1-butyl, 3-methylbutyl, 1-heptyl, 2-heptyl, or 3-heptyl.

Alternatively, when the polymers are copolymers the nanoparticle will comprise copolymeric compounds which comprise at least two different subunits. These subunits may be two or more different subunits according to formula 2A, or may be subunits according to formula 2A and other (different) subunits. The other subunits may be cyanoacrylate subunits, but may also be subunits formed from any other suitable co-monomers. Suitable co-monomers for use in forming the polymers of the invention are discussed further below.

The additional subunits may be cyanoacrylate subunits, such that the nanoparticle comprises copolymeric compounds which comprise (i) cyanoacrylate subunits according to formula 2A, and (ii) other (different) cyanoacrylate subunits. Preferably, these other cyanoacrylate subunits are cyanoacrylate subunits of formula 2B:

$$\begin{array}{c} \text{COOR}^3 \\ | \\ -\!\!\!+\!\!\text{C}-\!\!\text{CH}_2\!\!\frac{}{}_{n}\!- \\ | \\ \text{CN} \end{array} \quad (2B)$$

wherein each $R^3$ is independently selected from a group having from 1 to 15 non-hydrogen atoms, provided that $R^3$ is different to $R^1$. That is, $R^3$ may not be 2-ethylhexyl, 2-phenyl-ethyl, neopentyl, 1-pentyl, 2-pentyl, 3-pentyl, 3,3-dimethyl-1-butyl, 3-methylbutyl, 1-heptyl, 2-heptyl, or 3-heptyl.

Preferably, each of the non-hydrogen atoms are carbon atoms.

Each $R^3$ group may be linear or branched, and may include an aryl group.

More preferably, each $R^3$ is independently selected from a group having from 3 to 10 non-hydrogen atoms, more preferably from 5 to 8 non-hydrogen atoms.

Suitable $R^3$ groups include $C_{1-10}$ alkyl, $C_{1-10}$ alkenyl, $C_{1-10}$ alkynyl and $C_{1-8}$ alkyl-$C_{5-7}$ aryl.

Preferred $R^3$ groups include $C_{3-8}$ alkyl, $C_{3-8}$ alkenyl, $C_{3-8}$ alkynyl and $C_{1-5}$ alkyl-$C_{5-7}$ aryl.

More preferred $R^3$ groups include $C_{5-8}$ alkyl, $C_3$ alkynyl and $C_{1-3}$ alkyl-$C_6$ aryl.

Particularly suitable $R^3$ groups include 1-octyl, 1-butyl, 2-ethylbutyl, 4-methylpentyl, 1-hexyl, ethyl and propargyl, with propargyl being particularly preferred.

Preferably, the nanoparticle comprises copolymeric compounds which comprise two or more, preferably two, different cyanoacrylate subunits according to formula 2A.

In all of the embodiments of the invention described herein, unless otherwise stated it is preferred that 5% or more, more preferably 10% or more, even more preferably 30% or more, of the subunits in the polymer are cyanoacrylate subunits according to formula 2A.

In addition, in all of the embodiments of the invention described herein, unless otherwise stated it is preferred that 50% or more, more preferably 75% or more, more preferably 85% or more, even more preferably 95% or more, and most preferably 99% or more of the subunits in the polymer are cyanoacrylate subunits according to formula 2A or formula 2B, preferably formula 2A. Other subunits may be subunits formed from crosslinkers.

When the polymer is a homopolymer, all of the $R^2$ groups of formula 1 are the same, and are selected from one of the $R^1$ groups defined herein. Homopolymers where $R^1$ is 2-phenyl-ethyl or neopentyl are, however, solid at room temperature and pressure (25° C. and 1 atm). As such, it is preferred that when $R^1$ is 2-phenyl-ethyl or neopentyl, the polymers are copolymers.

It is therefore preferred that when $R^1$ is 2-phenyl-ethyl or neopentyl, the corresponding subunits represent between 5% and 50%, more preferably between 10% and 40%, of the subunits in the polymer. Put another way, in this case it is preferred that between 5% and 50%, more preferably between 10% and 40%, of the $R^2$ groups in formula 1 are 2-phenyl-ethyl or neopentyl.

As discussed above, the remaining subunits may be any suitable (different) subunit. However, other cyanoacrylate subunits are preferred, with different subunits of formula 2A or 2B being most preferred. That is, it is preferred that the remaining subunits are cyanoacrylate subunits of formula 2A wherein $R^1$ is other than 2-phenyl-ethyl or neopentyl, or cyanoacrylate subunits of formula 2B.

In contrast, when $R^1$ is 2-ethylhexyl, 1-pentyl, 2-pentyl, 3-pentyl, 3,3-dimethyl-1-butyl, 3-methylbutyl, 1-heptyl, 2-heptyl, or 3-heptyl, it is preferred that the corresponding subunits represent 50% or more, more preferably 75% or more, even more preferably 90% or more, and most preferably 95% or more of the subunits in the polymer. In this embodiment, it is preferred that all of the remaining subunits are subunits of formula 2A wherein $R^1$ is 2-phenyl-ethyl or neopentyl, or subunits of formula 2B.

Put another way, it may be preferred that 50% or more, more preferably 75% or more, even more preferably 90% or more, and most preferably 95% or more of the $R^2$ groups in formula 1 are 2-ethylhexyl, 1-pentyl, 2-pentyl, 3-pentyl, 3,3-dimethyl-1-butyl, 3-methylbutyl, 1-heptyl, 2-heptyl, or 3-heptyl.

Alcohol Toxicity

Different monomers have different toxicity in biological systems. This is in part due to the side chain of a cyanoacrylate, i.e. the alkyl or aryl-alkyl side chain, which will biodegrade to form different alcohols. Based on this knowledge, the inventors proposed that selection of an alcohol with low intrinsic toxicity could also affect the overall toxicity of PACA polymer nanoparticles.

It is known that the monomer has significant impact on the toxicity of otherwise similar nanoparticles (Lherm C et al, Int. J. Pharm. 1992; 84:13-22. doi: 10.1016/0378-5173(92)90210-S). The differences in cytotoxicity can be attributed to differences in the degradation rate and degradation products (alcohols) explained by rapidly-degrading nanoparticles resulting in a high local concentration of released polymer chains and alcohols. This would explain the observed higher toxicity of PBCA compared to PEBCA and POCA in prior art. However, as reported in Sulheim, 2017 (Sulheim et al, Int J Mol Sci. 2017 November; 18(11): 2454), the slowest degrading polymer of the three materials used, POCA, also caused the highest cytotoxic effect, while PEBCA, with an intermediate degradation, showed the lowest toxicity. The POCA toxicity may be explained by the high lipophilicity of octanol, which is more easily adsorbed by the cells than the more hydrophilic butanol and ethylhexanol. However, as explained in Sulheim, 2017 (Sulheim et al, Int J Mol Sci. 2017 November; 18(11): 2454) it was concluded that understanding the toxicity of nanoparticles is challenging, and that no single property can explain the observed toxic effects of PACA nanoparticles.

The inventors have selected and screened a number of alcohols for toxicity in relevant, international standard cell lines such as the human hepatocyte carcinoma, Hep G2 cell line and the porcine kidney epithelial cell line LLC-PK1 (see table 3). The results demonstrated variable toxicity. Alcohols that showed reduced toxicity in at least 1 cell line (as exemplified increased cell activity at 3% alcohol, when compared to OCA, BCA and EBCA controls, see table 3) were chosen as synthetic targets of interest for use in nanoparticle preparation. Note that although phenyl ethyl alcohol shows significant toxicity at 3% alcohol, it was selected for testing for structural features that could enable an improved range of active agents to be encapsulated in a novel PACA nanoparticles comprising the corresponding monomer. It was hypothesized that poly(phenyl ethyl cyanoacrylate), PPECA, may also improve API loading in some cases.

The results demonstrate that some alcohols are considerably less toxic than others (see table 3). Based on results of the toxicity tests, the most promising alcohols were determined, and the relevant ACA monomers (table 1) were chosen for synthesis of nanoparticles.

Empty particles were prepared by a standard mini-emulsion polymerization method for determination of particle toxicity against international standard cell lines (Hep G2 and LLC-PK1). The particles were formed from the monomers 2-ethylhexyl (2-EHCA), 2-phenyl ethyl (2-PECA), neopentyl (NPCA), 1-pentyl (1-PCA), 2-pentyl (2-PCA), 3-pentyl (3-PCA), 3,3-dimethyl-1 butyl (3,3-DMBCA), 1-heptyl (1-HPCA), 2-heptyl (2-HPCA), 3-heptyl (3-HPCA) or 3-methylbutyl (3-MBCA) cyanoacrylate. Particles made of 1-butyl cyanoacrylate (BCA), 1-octyl cyanoacrylate (OCA) and 2-ethyl butyl cyanoacrylate (EBCA) were used as controls. Results are reported as the concentration required to reduce cell activity by 50% (1050) and vary a little from cell line to cell line. The tests demonstrated that of the monomers known in the prior art, polymers formed from EBCA are 2× less toxic than polymers formed from BCA which are slightly less toxic than polymers formed from OCA. The toxicity of the empty particles is important because the more particle that can be used without toxicity, the more active agent can be delivered without risking unwanted side effects.

The provided nanoparticles comprising polymers formed from 2-ethylhexyl (2-EHCA), 2-phenyl-ethyl (PECA), neopentyl (NPCA), 1-pentyl (1-PCA), 3,3-dimethyl-1 butyl (3,3-DMBCA), 1-heptyl (1-HPCA), 2-heptyl (2-HPCA), 3-heptyl (3-HPCA) or 3-methylbutyl (3-MBCA) cyanoacrylates all demonstrated lower toxicity compared to market leaders, such as nanoparticles comprising polymers formed from OCA.

In particular, the tests demonstrated in different cell lines that polymers formed from cyanoacrylate monomers selected from the group consisting 2-EHCA, 1-HPCA and 3-MPCA exhibit lower or similar toxicity compared to polymers formed from the commonly used OCA, BCA, 2-EBCA (see table 2).

The results also show that PECA can be blended into particles up to 33% without affecting toxicity of the particles.

TABLE 2

Particle Toxicity, MTT and LDH tests in different cell lines.

| Standard Monomer blend | Particle Toxicity MTT test IC50 (µg/ml particles) | | Particle Toxicity LDH test IC50 (µg/ml particles) | |
|---|---|---|---|---|
| | Hep G2 | LLC-PKI | Hep G2 | LLC-PKI |
| 2-EHCA | 300 | 240 | >300 | 205 |
| 1:2 (2-PECA):BCA | 25 | 24 | 33 | 8 |
| 1:2 NPCA:BCA | 22 | 26 | >300 | 16 |
| 3-HPCA | 18 | 8 | >300 | 8 |
| 3-MBCA | 48 | 24 | 65 | 9 |
| 1-HPCA | 67 | 62 | 68 | 40 |
| 2-HPCA | 43 | 15 | 50 | 15 |
| 1-PCA | 26 | 14 | 32 | 20 |
| 3,3-DMBCA | 40 | 18 | 48 | 18 |
| OCA (control) | 32 | 17 | 300 | 12 |
| EBCA (control) | 43 | 48 | 95 | 73 |
| BCA (control) | 24 | 20 | 29 | 26 |

Due to their relatively low toxicity, as shown in the results in table 2, it may be preferred that the nanoparticles comprise copolymeric or homopolymeric compounds which comprise cyanoacrylate subunits according to formula 2A, where each $R^1$ is independently selected from the group consisting of 2-ethylhexyl, 2-phenyl-ethyl, neopentyl, 1-pentyl, 3,3-dimethyl-1-butyl, 3-methylbutyl, 1-heptyl, 2-heptyl, and 3-heptyl.

Preferably, each $R^1$ is independently selected from the group consisting of 2-ethylhexyl, neopentyl, 3-methylbutyl, 1-heptyl, and 3-heptyl.

More preferably, each $R^1$ is independently selected from the group consisting of 2-ethylhexyl, 3-methylbutyl, and 1-heptyl; or the group consisting of 2-ethylhexyl, neopentyl, and 3-heptyl.

Even more preferably, each $R^1$ is independently selected from the group consisting of 2-ethylhexyl and 1-heptyl.

Most preferably, $R^1$ is 2-ethylhexyl.

TABLE 3

Results from alcohol toxicity assay.
Given as remaining activity
(%) in cell line at 3.00 wt % alcohol

| Alcohol | Cell activity remaining at 3.00 wt % alcohol (%) | | |
|---|---|---|---|
| | IMR-90 | Hep G2 | LLC-PK1 |
| 1-octanol (control) | 0.9 | 69.8 | 1.8 |
| 2-ethylbutanol (control) | 69.1 | 74.6 | 86.2 |
| 1-butanol (control) | 59.7 | 61.8 | 81.8 |
| 2-ethylhexanol | 7.9 | 91.2 | 79.8 |
| 2-phenylethanol | 0.6 | 0.9 | 1.1 |
| 1-heptanol | 58.3 | 72.3 | 61.8 |
| 2-heptanol | 50.7 | 73.9 | 81.1 |

TABLE 3-continued

Results from alcohol toxicity assay.
Given as remaining activity
(%) in cell line at 3.00 wt % alcohol

| Alcohol | Cell activity remaining at 3.00 wt % alcohol (%) | | |
|---|---|---|---|
| | IMR-90 | Hep G2 | LLC-PK1 |
| 3-heptanol | 81.7 | 81.4 | 96.4 |
| 1-pentanol | 57.1 | 63.3 | 83.4 |
| 3-pentanol | 84.6 | 89.7 | 78.6 |
| 3-methylbutanol | 67.6 | 72.4 | 94.3 |
| 3,3-dimethylbutanol | 81.7 | 84.8 | 98.2 |

Due to the low toxicity of the corresponding alcohols shown in table 3, it may be preferred that the nanoparticles comprise copolymeric or homopolymeric compounds which comprise cyanoacrylate subunits according to formula 2A, where each $R^1$ is independently selected from the group consisting of 2-ethylhexyl, 1-pentyl, 3-pentyl, 3,3-dimethyl-1-butyl, 3-methylbutyl, 1-heptyl, 2-heptyl, and 3-heptyl.

More preferably, each $R^1$ is independently selected from the group consisting of 3,3-dimethyl-1-butyl, 3-methylbutyl, and 3-heptyl; or the group consisting of 2-ethylhexyl, 3-pentyl, 3,3-dimethyl-1-buty, and 3-heptyl; or the group consisting of 3-pentyl, 3,3-dimethyl-1-butyl, and 3-heptyl.

Even more preferably, each $R^1$ is independently selected from the group consisting of 3,3-dimethyl-1-butyl, and 3-heptyl.

Polymerizable Cyanoacrylate Monomers

The nanoparticles of the present invention comprise polymers formed from cyanoacrylate monomers, which polymerize to form said polymers. The use of these monomers to prepare biodegradable polymers in the preparation of nanoparticles has been widely reported. The cyanoacrylate may be a monofunctional or difunctional acrylate i.e. containing a single or multiple acrylate functionality.

In the case of the present invention, certain straight or branched chain alkyl cyanoacrylate monomers and aryl substituted alkyl cyanoacrylates, have proved to be advantages compared to OCA/BCA/EBCA. Preferred monomers are those of $C_5$ or $C_7$ and selected $C_8$ ACA. A single monomer may be used, or mixtures of different ACA may be used.

Preferred ACA include 2-ethylhexyl (2-EHCA), 2-phenyl ethyl (2-PECA), neopentyl (NPCA), 1-pentyl (1-PCA), 2-pentyl (2-PCA), 3-pentyl (3-PCA), 3,3-dimethyl-1 butyl (3,3-DMBCA), 1-heptyl (1-HPCA), 2-heptyl (2-HPCA), 3-heptyl (3-HPCA) or 3-methylbutyl (3-MBCA) cyanoacrylates.

Different choices for the side chain open variability for the physical and physiological properties of the nanoparticle. In particular, it has been demonstrated that both the loading capacity and the range of active agents to be encapsulated is affected by the choice of ACA used when producing the nanoparticles.

As explained above, the preferred ACAs demonstrate a lower toxicity in in vitro studies compared to previously known monomers that are used in preparation of PACA nanoparticles, such as OCA, BCA and EBCA. The toxicity and performance were compared to initial alcohol toxicity results and compared to one example of a market leader in use for drug delivery today, namely 2-ethylbutyl cyanoacrylate (PEBCA). As demonstrated, surprisingly good results in view of toxicity compared to PEBCA can be obtained when nanoparticles include polymers formed from ACAs belonging to the group consisting of 2-ethylhexyl (2-EHCA), 3-methylbutyl (3-MBCA) and 1-heptyl (1-HPCA).

Thus, in one embodiment, the nanoparticles of the invention comprise copolymeric or homopolymeric compounds which comprise cyanoacrylate subunits according to formula 2A, where each $R^1$ is independently selected from the group consisting of 2-ethylhexyl, 3-methylbutyl and 1-heptyl.

Without wishing to be bound by theory, it is believed that the nature of the monomers also influences the degradation rate of the polymer. The more hydrophobic the monomer (i.e. the longer the alkyl chain), the slower the degradation rate, probably due to a lower water level in more hydrophobic polymers.

Hence, in another embodiment it is provided a mixture (a blend) of ACAs of differing chain length, e.g. one with a short alkyl chain and one with a long alkyl chain, such as 2-EHCA with 1-PCA. A blend of different monomers also enables different properties to be achieved for the final particles.

Thus, in one embodiment, the nanoparticles of the invention comprise copolymeric compounds which comprise (i) cyanoacrylate subunits according to formula 2A where $R^1$ is 2-ethylhexyl; and (ii) cyanoacrylate subunits according to formula 2A where $R^1$ is 1-pentyl.

It has also been demonstrated that all the selected new monomers blend well with propargyl cyanoacrylate, PPCA. Accordingly, the invention includes a polymer formed from a mix of any of 2-ethylhexyl (2-EHCA), 2-phenyl ethyl (2-PECA), neopentyl (NPCA), 1-pentyl (1-PCA), 2-pentyl (2-PCA), 3-pentyl (3-PCA), 3,3-dimethyl-1 butyl (3,3-DMBCA), 1-heptyl (1-HPCA), 2-heptyl (2-HPCA), 3-heptyl (3-HPCA) or 3-methylbutyl (3-MBCA) cyanoacrylates with propargyl cyanoacrylate, PPCA.

Thus, the nanoparticles may comprise copolymeric compounds which comprise (i) cyanoacrylate subunits according to formula 2A (where $R^1$ is as defined herein); and (ii) cyanoacrylate subunits according to formula 2B where $R^3$ is propargyl (i.e. —$CH_2$—C≡CH).

When present, it is preferred that less than 25%, more preferably from 0.5% to 15%, and even more preferably from 1% to 10%, of the subunits are cyanoacrylate subunits according to formula 2B where $R^3$ is propargyl.

Thus, it is preferred that 75% or more, more preferably from 85% to 99.5%, and even more preferably from 90% to 99%, of the subunits are cyanoacrylate subunits according to formula 2A.

As an example, polymers comprising such blends of subunits enable production of nanoparticles for use with a copper based click reaction to functionalise the resulting PACA nanoparticles. This is a great advantage as this allows for targeting of the nanoparticles, such as active targeting by incorporation of a targeting moiety.

The nanoparticles may comprise a mixture of ACAs that have different types of organic side groups. Different organic side groups include for example side groups comprising an alkyl chain and/or an aryl group. 2-PECA is a monomer particularly interesting for this purpose, as 2-PECA is preferably blended with a co-monomer as it is a solid. Due to its structure, a mixture comprising 2-PECA can enhance the solubility of selected active agent.

Preferred nanoparticles comprise polymers formed from a mixture of 2-PECA blended with an ACA selected from the group consisting of 2-ethylhexyl (2-EHCA), neopentyl (NPCA), 1-pentyl (1-PCA), 2-pentyl (2-PCA), 3-pentyl (3-PCA), 3,3-dimethyl-1 butyl (3,3-DMBCA), 1-heptyl (1-HPCA), 2-heptyl (2-HPCA), 3-heptyl (3-HPCA) or 3-methylbutyl (3-MBCA) cyanoacrylates. Particularly preferred are nanoparticles according to the invention comprising polymers formed from 2-phenyl ethyl cyanoacrylate (2-PECA) blended with 2-EHCA or 1-HPCA.

Other preferred nanoparticles comprise or consist of cyanoacrylate homopolymers formed from a single monomer selected from the group of 2-ethylhexyl (2-EHCA), 1-pentyl (1-PCA), 2-pentyl (2-PCA), 3-pentyl (3-PCA), 3,3-dimethyl-1 butyl (3,3-DMBCA), 1-heptyl (1-HPCA), 2-heptyl (2-HPCA), 3-heptyl (3-HPCA) or 3-methylbutyl (3-MBCA) cyanoacrylates.

In another embodiment it is provided a nanoparticle that comprises or consists of a cyanoacrylate copolymer, i.e. a nanoparticle formed from at least two monomers. Of the total amount of ACA monomers, a first and a second ACA monomer are mixed, wherein the first monomer is preferably present in an amount of 1 to 99 wt % of the total amount of monomers used.

In yet another embodiment, the first ACA monomers are preferably present in an amount of 65 to 99 wt %, more preferably 67-99%, more preferably 75-99 wt %, even more preferably 95-99 wt % of the total amount of monomers.

In addition to the selected ACA monomers, the nanoparticles may also comprise polymers formed from other co-monomers. It is preferable if these co-monomers are also biocompatible or biodegradable. Suitable co-monomers include, but are not limited to acrylates, vinyl esters, vinyl ethers, vinyl epoxides, cyclic siloxanes and lactones. Said co-monomers may also be crosslinkers depending on the desired particle properties.

The crosslinker is preferably an anhydride, an acrylate or a bis-cyanoacrylate, such as mono- or polyethylene glycol dimethacrylate, methacrylic anhydride, 1,6-hexanediol bis-cyanoacrylate or methylene dimethacrylate.

The polymerisable monomers, such as the cyanoacrylate monomers (e.g. the monomers of formula 2), preferably comprise from 25 to 99.5 wt. % of the oil phase, more preferably from 30 to 70 wt. %.

Selected Active Agents

The nanoparticles of the invention are loaded with an active agent, i.e. an active agent is encapsulated within the nanoparticle. The active agent can be a therapeutic agent or a diagnostic agent. Therapeutic agents are often referred to as an API, i.e. an active pharmaceutical agent. Due to the degree of solubility with the monomers used to prepare the nanoparticles of the present invention, it is possible to encapsulate a broad range of active agents.

The active agent may be an anti-cancer agent, an anti-infection agent, a central nervous system agent (i.e. a drug with affects the central nervous system), an anti-inflammatory agent, or a diagnostic/imaging agent.

The active agent is preferably an anti-cancer agent, an anti-infection agent (e.g. an antimicrobial agent), a central nervous system agent or a diagnostic/imaging agent.

More preferably, the active agent is an anti-cancer agent, an anti-infection agent (e.g. an antimicrobial agent), or a diagnostic/imaging agent.

Suitable anti-cancer agents include taxanes (such as cabazitaxel and docetaxel), platins or platinum-based antineoplastic drugs (such as cisplatin, oxaliplatin, and carboplatin, preferably oxaliplatin), histone deacetylase inhibitors (such as belinostat), and phosphoinositide 3-kinase inhibitors (such as alpelisib).

Suitable anti-infection agents include antimicrobial agents and antifungal agents. Preferred anti-infection agents are antimicrobial agents, preferably antibacterial agents such as mupirocin.

Suitable diagnostic/imaging agents include stains, preferably lipophilic stains such as Nile red (for example NR668).

More preferably, the active agent is an anti-cancer agent, an antibacterial agent or a diagnostic/imaging agent.

Even more preferably, the active agent is an anti-cancer agent or a diagnostic/imaging agent.

Most preferably, the active agent is an anti-cancer agent.

The active agent may be selected from the group consisting of alpelisib; a taxane, such as cabazitaxel and docetaxel; a platin, such as oxaliplatin; mupirocin; belinostat; Nile red; or NR668. Taxanes such as cabazitaxel are particularly preferred.

The total amount of active agent is preferably from 0.2 to 50 wt. % of the oil phase, more preferably from 0.2 to 30 wt. %. Thus, the nanoparticle preferably comprises from 0.2 to 50 wt. % active agent, more preferably from 0.2 to 30 wt. % active agent.

When the active agent is an therapeutic agent (e.g. an anti-cancer agent, a central nervous system agent, or an anti-infection agent), the total amount of active agent is preferably from 1.0 to 50 wt. % of the oil phase, more preferably from 2.5 to 40 wt. % and even more preferably from 5 to 30 wt. %. In this case, the nanoparticle therefore preferably comprises from 1.0 to 50 wt. % active agent, more preferably from 2.5 to 40 wt. % active agent, and even more preferably from 5 to 30 wt. % active agent.

When the active agent is a diagnostic or imaging agent (e.g. a stain), the total amount of active agent is preferably from 0.2 to 50 wt. % of the oil phase, more more preferably from 0.2 to 20 wt. %. In this case, the nanoparticle therefore preferably comprises from 0.2 to 50 wt. % active agent, more preferably from 0.2 to 20 wt. % active agent.

Method for Making Nanoparticles by Miniemulsion

In a preferred embodiment, the nanoparticles of the present invention are produced by a method comprising anionic polymerisation of an oil-in water miniemulsion.

Miniemulsion processes are known for the production of nanoparticles with average sizes typically in the range 1-1000 nm, such as 30-500 nm, as disclosed e.g. in Landfester in Macromol. Rapid Comm. 2001, 22, 896-936 and Landfester et al in Macromolecules 1999, 32, 5222-5228. The method was first described by Ugelstad et al. (1973) Emulsion polymerization: initiation of polymerization in monomer droplets. *J Polym Sci Polym Lett Ed* 11:503-513.

The miniemulsion technique for the preparation of polymeric nanoparticles is a technology by which a dispersion is prepared, by converting a stable nanoemulsion of a dispersed phase in a continuous phase into a nanoparticle dispersion by polymerisation reactions. The technology involves mixing the various components in the dispersed phase before emulsification with the continuous phase takes place, resulting in the production of an emulsion in which each droplet has an identical composition of active agent and monomers.

All types of polymerisation reactions may be applied in these droplet nanoreactors. In the case of poly(alkyl cyanoacrylate) nanoparticles, oil-in-water miniemulsions and anionic polymerisation at the droplet interface, commonly started by adding an initiator to the continuous phase, have proved to be advantageous. The particles formed are typically identical or almost identical to the droplets from which they are prepared, in terms of size and size distribution, resulting in high reproducibility of the process.

As used herein, the term "miniemulsion" means a specific type of emulsion comprising stable droplets with typical mean sizes within the range 30 to 500 nm. The particle size is influenced by a number of factors, including the amount of surfactant present, the viscosity of the system as a whole and the shear rate used to produce the droplets. Typical particle size distribution curves (measured using, for example, dynamic light scattering) for miniemulsions are Gaussian in shape and are relatively narrow. The miniemulsions preferably have a polydispersity index (PDI) of 0.3 or less, more preferably 0.2 or less, such as about 0.1.

Miniemulsions are ideally stabilised by the presence of a surfactant and a co-stabiliser, the latter often referred to as "hydrophobe". The co-stabiliser contributes to the osmotic stabilisation of the emulsion by increasing the osmotic pressure, which counteracts the capillary or Kelvin pressure due to surface tension of the droplets and reduces Ostwald ripening. Ostwald ripening refers to the process by which molecules diffuse from small droplets to large ones through the continuous phase. This process disrupts the emulsion structure. Miniemulsions may be direct (oil-in-water) or inverse (water-in-oil) although for the purposes of this embodiment of the present invention, the term "miniemulsion" may be considered to refer only to direct miniemulsions. In such miniemulsions, water forms the continuous phase. The oil phase typically contains the monomers used in the anionic polymerisation, the co-stabiliser and the active agent, i.e. the loading compound of interest, if present.

As discussed above, miniemulsions and miniemulsion polymerisation for the preparation of nanoparticles are known in the art.

The miniemulsion may be prepared by any known method in the art, such as that described in US 2009/0297613. Processes typically involve forming the oil and water phases, mixing these and subjecting the mixture to high shear forces, e.g. ultrasonication or homogenisation, to form a stable emulsion of oil droplets containing the monomer with a stabiliser/surfactant on the surface, and then subsequently adding a hydrophilic initiator. Polymerisation of the monomer droplets then occurs by initiation at the droplet interface to form polymeric particles which have the same size as the droplets before polymerisation. The hydrophilic initiator is attached to the surface of the particles. Alternatively, polymerisation is initiated by adjustment of the pH. It should be apparent to the skilled worker that the miniemulsion polymerisation processes described in the context of this embodiment of the present invention are quite distinct from emulsion polymerisation processes whereby polymeric nanoparticles are formed directly from a solution of the monomers in a solvent and from emulsion processes using pre-made polymers, whereby the polymeric nanoparticles are formed by self-assembly of these pre-made polymers.

The miniemulsions may comprise at least three components: polymerizable monomers comprising at least one ACA monomer; at least one surfactant, selected from any possible surfactant, not limited to, polysaccharides, biopolymers, PEG, PPG, dextrans preferably a polyalkylene glycol selected from polyethylene glycols (PEGs) and polypropylene glycols (PPGs), or mixtures thereof, and optionally an inhibitor. The miniemulsions may also optionally comprise one or more active agents. In one embodiment of the invention, at least one of said surfactants, e.g. at least one polyalkylene glycol, initiates the anionic polymerisation of the polymerisable monomers.

The inhibitor may be an anionic and/or a radical inhibitor. Thus, the inhibitor may be an anionic inhibitor, which may be used alone or in combination with a radical inhibitor. Alternatively, the inhibitor may be a radical inhibitor, which may be used alone or in combination with an anionic inhibitor. Alternatively, the inhibitor may be a dual-action anionic and radical inhibitor. Preferably, the inhibitor comprise 0.05 to 15 wt % of the miniemulsion, even more preferred, the inhibitor is in the range of 0.1 to 10 wt % or 0.5 to 6 wt %.

The miniemulsions of this embodiment of the invention may comprise at least one surfactant. Any typical surfactant known in the art may be used, however preferable surfactants include fatty acids of glycerols, sorbitol and other multifunctional alcohols, poloxamers, poloxamines, polysorbates, polyoxyethylene ethers and polyoxyethylene esters, ethoxylated triglycerides, ethoxylated phenols and diphenols, polysaccharides (e.g. hyaluronic acid and sialic acid), proteins, metal salts of fatty acids, metal salts of fatty alcohol sulfates, sodium lauryl sulfate, metal salts of sulfosuccinates and mixtures thereof. Particularly preferred surfactants include polyoxyethylene ethers and polysorbates.

The surfactant preferably comprises 0.05 to 5 wt % of the miniemulsion, more preferably 0.1 to 2 wt %.

In addition to these components, the miniemulsion may further comprise a co-stabiliser in the oil phase. The co-stabiliser is typically highly water insoluble, i.e. has a solubility of less than $5 \times 10^{-5}$ mol/L, more preferably less than $5 \times 10^{-6}$ mol/L and still more preferably less than $5 \times 10^{-7}$ mol/L and may be any substance which is compatible with the polymerisable monomer(s), such as a hydrocarbon, silane, organosilane, fatty acid ester, oil (e.g. plant oil), hydrophobic dye or lipid. Examples of suitable co-stabilisers include hexadecane, cetyl alcohol, miglyol and olive oil. Particularly preferred co-stabilisers include miglyols and plant oils. In an alternative embodiment, the active agent may perform the role of the co-stabiliser.

The co-stabiliser preferably comprises 0.5 to 5 wt % of the oil phase, more preferably 1 to 3 wt %.

In a further embodiment the miniemulsion used in the described process comprises a crosslinker (especially a biodegradable crosslinker), preferably in the oil phase (i.e. the discontinuous phase). The crosslinker is preferably an anhydride, an acrylate or a bis-cyanoacrylate, such as mono- or polyethylene glycol dimethacrylate, methacrylic anhydride, 1,6-hexanediol bis-cyanoacrylate or methylene dimethacrylate.

The oil phase content of the miniemulsions of this embodiment may be up to 50%, but is typically up to 15-25 wt %, preferably up to 15 wt % or in the range of 5-15 wt %. The skilled person will understand that the oil phase content of the mini-emulsions of this embodiment may also be referred to as the solid content. Thus, the terms "solid content" and "oil phase content" are interchangeable in the context of the miniemulsion technique.

The nanoparticles of the present invention may alternatively be produced by a method comprising the radical polymerisation of an oil-in water miniemulsion. The above discussion relating to anionic polymerisation applies mutatis mutandis to this embodiment.

Other Methods for Making Nanoparticles

Whilst the miniemulsion method using anionic polymerisation demonstrate the applicability of the monomers in the examples, the new monomers can be applied to any nanoparticle synthesis method previously reported for ACA monomers, for example (and not limited to) emulsion polymerisation, self-assembly and nanoprecipitation. Both anion and radical initiation can be used.

Loading Capacity and Range of Active Agent

In the case of nanoparticles prepared by the miniemulsion method, the technology involves mixing the various components in the dispersed phase before emulsification with the continuous phase takes place, resulting in the production of an emulsion in which each droplet has an identical composition of active agent and monomers. The particles formed are typically identical or almost identical to the droplets from which they are prepared. By applying this technique, the loading capacity of the nanoparticle is influenced by the interaction between the side chain of the cyanoacrylates and the active agent to be encapsulated in the nanoparticle and has been demonstrated to be particularly high.

Variations in the side chain (i.e. variation in the $R^1$ group of the subunits of formula 2A) will affect the hydrophobicity and hydrophilicity of the subunits, and hence the interaction between the side chain of the subunit and the active agent (e.g. API). Increased interaction between these components will enhance the concentration of active agent (e.g. API) that is achievable to encapsulate in the different nanoparticles.

Accordingly, if a hydrophobic active agent (e.g. API) is to be encapsulated, side chains that interact well with a hydrophobic active agent (e.g. API) must be chosen. Examples of this are encapsulation of cabazitaxel or alpelisib in a nanoparticle formed from any of 2-ethylhexyl (2-EHCA), 2-phenyl ethyl (2-PECA), neopentyl (NPCA), 1-pentyl (1-PCA), 2-pentyl (2-PCA), 3-pentyl (3-PCA), 3,3-dimethyl-1 butyl (3,3-DMBCA), 1-heptyl (1-HPCA), 2-heptyl (2-HPCA), 3-heptyl (3-HPCA) or 3-methylbutyl (3-MBCA) cyanoacrylates.

Preferably therefore, the active agent used in the present invention is hydrophobic.

On the other hand, if a hydrophilic active agent (e.g. API) is to be encapsulated, a monomer with side chains that interact well with a hydrophilic active agent (e.g. API) can be chosen.

Higher concentration of active agent (e.g. API) gives the effect that lower concentrations of nanoparticles can be used, leading to fewer or less severe side effects.

Similarly, the inclusion of different functional groups, such as an aromatic ring, in the side chain also changes the types of interactions available between side chain and the active agent (e.g. API), e.g. by allowing for π-π interactions. This affects particle stability and particle formation with some payload. An example of this is encapsulation of oxaliplatin in a blend of PECA and BCA, which is not possible with BCA alone. Thus, the range of active agents can be broadened by the inclusion of for example 2-PECA, which has been demonstrated to solubilize an improved range of active agents. This offers significant improvement over the prior art.

Thus, the nanoparticles may comprise copolymeric or homopolymeric compounds which comprise cyanoacrylate subunits according to formula 2A, wherein $R^1$ is 2-phenyl-ethyl. As discussed above, it is preferred that when $R^1$ is 2-phenyl-ethyl, the polymer is a copolymer. That is, the nanoparticles comprise copolymeric compounds which comprise cyanoacrylate subunits according to formula 2A wherein $R^1$ is 2-phenyl-ethyl. Since the polymer is a copolymer, other subunits must also be present.

In this case it is preferred that between 5% and 50%, more preferably between 10% and 40%, of the subunits in the polymer are cyanoacrylate subunits according to formula 2A wherein $R^1$ is 2-phenyl-ethyl.

The other subunits may be any suitable subunits, including other cyanoacrylate subunits. For example, the copolymer may comprise (i) cyanoacrylate subunits according to formula 2A wherein $R^1$ is 2-phenyl-ethyl, and (ii) cyanoacrylate subunits according to formula 2B, as defined above.

For example, the copolymer may comprise (i) cyanoacrylate subunits according to formula 2A wherein $R^1$ is 2-phenyl-ethyl, and (ii) cyanoacrylate subunits according to formula 2B wherein $R^3$ is 1-butyl. In this case, the active agent is preferably a platin, more preferably oxaliplatin.

Alternatively the copolymer may comprise (i) cyanoacrylate subunits according to formula 2A wherein $R^1$ is 2-phenyl-ethyl, and (ii) cyanoacrylate subunits according to formula 2A wherein each $R^1$ is independently selected from 2-ethylhexyl, neopentyl, 1-pentyl, 2-pentyl, 3-pentyl, 3,3-dimethyl-1-butyl, 3-methylbutyl, 1-heptyl, 2-heptyl, and 3-heptyl.

For example, the copolymer may comprise (i) cyanoacrylate subunits according to formula 2A wherein $R^1$ is 2-phenyl-ethyl, and (ii) cyanoacrylate subunits according to formula 2A wherein each $R^1$ is independently selected from 2-ethylhexyl and 1-heptyl, preferably 2-ethylhexyl. In this case, the active agent is preferably a platin, more preferably oxaliplatin.

Variations in active agent (e.g. API) solubility are exemplified but not limited to the APIs given in table 4. The broadening of the API range is exemplified by the use of a PECA/BCA blend to dissolve and hence produce PACA nanoparticles containing oxaliplatin, a platinum API for the first time (π-π interactions). The variation in active agent solubility in monomers with alkyl side chains of differing length and substitution pattern is exemplified by the solubility of mupirocin, which is insoluble in the controls (EBCA, OCA and BCA), but soluble in 3-PCA and in 2-HPCA. Similarly, belinostat is soluble in 2-EHCA, but not in the control 2-EBCA. On the other hand, alpelisib and cabazitaxel are soluble in all ACAs tested.

As shown by the data in Table 4, of the controls only BCA was able to dissolve alpelisib, and could therefore be used to prepare alpelisib loaded nanoparticles. However, all of the exemplary monomers and monomer blends were able to dissolve alpelisib, and were therefore suitable to prepare alpelisib loaded nanoparticles.

The invention therefore provides nanoparticles as defined herein, wherein the nanoparticles contain alpelisib or cabazitaxel as the active agent, more preferably alpelisib.

It was also found that none of the controls was able to dissolve mupirocin, whereas 3-PCA and 2-HPCA were both able to dissolve mupirocin.

The invention therefore provides nanoparticles comprising copolymeric or homopolymeric compounds which comprise cyanoacrylate subunits according to formula 2A, wherein each $R^1$ is independently 3-pentyl or 2-heptyl. Preferably, in this case the nanoparticles contain mupirocin as the active agent.

The invention provides nanoparticles comprising copolymeric or homopolymeric compounds which comprise cyanoacrylate subunits according to formula 2A, wherein $R^1$ is 3-pentyl, and the nanoparticles contain mupirocin as the active agent.

The invention provides nanoparticles comprising copolymeric or homopolymeric compounds which comprise cyanoacrylate subunits according to formula 2A, wherein $R^1$ is 2-heptyl, and the nanoparticles contain mupirocin as the active agent.

The invention provides nanoparticles comprising copolymeric or homopolymeric compounds which comprise cyanoacrylate subunits according to formula 2A, wherein $R^1$ is 1-heptyl. Preferably, in this case the nanoparticles contain docetaxel as the active agent.

The invention provides nanoparticles comprising copolymeric or homopolymeric compounds which comprise cyanoacrylate subunits according to formula 2A, wherein each $R^1$ is independently 2-ethylhexyl or 1-heptyl. Preferably, in this case the nanoparticles contain belinostat as the active agent.

It was also surprisingly found that a blend of PECA and BCA monomers or PECA and 2-EHCA monomers was able to dissolve oxaliplatin, and hence produce PACA nanoparticles containing oxaliplatin, a platinum-based API for the first time. Without wishing to be bound by theory, it is believed that this is due to π-π interactions from the PECA.

The invention therefore provides nanoparticles comprising copolymeric compounds which comprise cyanoacrylate subunits according to formula 2A, wherein $R^1$ is 2-phenyl-ethyl; wherein the nanoparticles comprise a platin (preferably oxaliplatin) as the active agent.

The nanoparticles of the invention demonstrate that an improved range of active agents can be encapsulated. It has been demonstrated that 2-PECA dissolves cabazitaxel (CBZ), alpelisib and oxaliplatin (see table 4).

Thus, the nanoparticles may comprise copolymeric or homopolymeric compounds which comprise cyanoacrylate subunits according to formula 2A wherein $R^1$ is 2-phenyl-ethyl, wherein the active agent is selected from the group consisting of alpelisib, a taxane, such as cabazitaxel and docetaxel, a platin, such as oxaliplatin, mupirocin and belinostat. Preferably, in this case the active agent is oxaliplatin, cabazitaxel or alpelisib.

As described herein, the miniemulsion technique may be used to produce nanoparticles according to the invention. In addition to the other ingredients, the miniemulsion can further comprises a co-stabiliser in the oil phase, which has been shown to affect the stability of the dispersion prior to polymerisation as well as the particle stability. When miniemulsions are used, the ability to produce a stabile dispersion before polymerization takes place may also be affected by the presence of active agents to be incorporated into the nanoparticle, as the active agent may perform the role of the co-stabiliser. As described in the prior art, a particular high loading of cabazitaxel has successfully been incorporated into PEBCA nanoparticles. Without being bound by theory, it is hypostasized that the high loading is due to cabazitaxel taking the part as a co-stabilizer in the reaction.

However, the active agent may also be reactive, thus being counter-effective for the stability of miniemulsion and the prepared nanoparticle.

The solubility of different drugs with different cyanoacrylate monomers also influence the amount of drug that can be encapsulated in the nanoparticles. Thus, the nanoparticles of the invention has the advantage of improved active loading.

TABLE 4

The solubility of different active agents, in ACA monomers.

| Monomer blend | Solubility | | | | | |
|---|---|---|---|---|---|---|
| | CBZ | Alpelisib | Mupirocin | Oxaliplatin | Docetaxil | Belinostat |
| OCA (control) | Soluble | Not tested | Insoluble | Insoluble | Not tested | Not tested |
| EBCA (control) | Soluble | Not tested | Insoluble | Insoluble | Not tested | Insoluble |

TABLE 4-continued

The solubility of different active agents, in ACA monomers.

| Monomer blend | Solubility | | | | | |
|---|---|---|---|---|---|---|
| | CBZ | Alpelisib | Mupirocin | Oxaliplatin | Docetaxil | Belinostat |
| BCA (control) | Soluble | Soluble | Insoluble | Insoluble | Soluble | Not tested |
| 2-EHCA | Soluble | Soluble | Partially | Insoluble | Insoluble | Soluble |
| 1:2 (2-PECA):BCA | Soluble | Soluble | Insoluble | Soluble | Not tested | Not tested |
| 1:2 NPCA:BCA | Soluble | Soluble | Insoluble | Insoluble | Not tested | Not tested |
| 1:2 (2-PECA):(2-EHCA) | Not tested | Not tested | Not tested | Soluble | Not tested | Not tested |
| 3-HPCA | Soluble | Soluble | Partially | Insoluble | Not tested | Not tested |
| 3-MBCA | Soluble | Soluble | Insoluble | Insoluble | Not tested | Not tested |
| 1-HPCA | Soluble | Soluble | Insoluble | Insoluble | Soluble | Soluble |
| 2-HPCA | Soluble | Soluble | Soluble | Insoluble | Not tested | Not tested |
| 1-PCA | Soluble | Soluble | Insoluble | Insoluble | Not tested | Not tested |
| 3-PCA | Soluble | Soluble | Soluble | Insoluble | Not tested | Not tested |
| 3,3-DMBCA | Soluble | Soluble | Insoluble | Insoluble | Not tested | Not tested |

Efficacy

All cyanoacrylate monomers selected from the group consisting of 2-ethylhexyl (2-EHCA), 2-phenyl ethyl (2-PECA), neopentyl (NPCA), 1-pentyl (1-PCA), 2-pentyl (2-PCA), 3-pentyl (3-PCA), 3,3-dimethyl-1 butyl (3,3-DMBCA), 1-heptyl (1-HPCA), 2-heptyl (2-HPCA), 3-heptyl (3-HPCA) or 3-methylbutyl (3-MBCA) could be used to prepare efficacious particles (see table 5).

It is also noted that less toxic particles with a greater loading capacity and similar efficacy, will improve the risk/benefit ratio in favour of the patient Thus, a great advantage with the invention as described herein is that it provides a new range of nanoparticles comprising monomer which can be selected based both on the toxicity of the resulting particle and the solubility of the API.

TABLE 5

Data from successful example, nanoparticle batches.

| Monomer blend | Encapsulated API | Z-ave Size pH 7 (nm) | PDI | Zeta potential pH 7 (mV) | Dry Weight (%) | Drug Conc. % (w/w) | Particle efficacy, cell Glo assay IC50 (µg/ml) A546 | Du-145 |
|---|---|---|---|---|---|---|---|---|
| OCA (control) | — | 85.37 | 0.156 | −1.99 | 5.07 | | 26.100 | 12.500 |
| OCA (control) | Cabazitaxel | 147.2 | 0.37 | −2.21 | 5.31 | 3.96 | 0.125 | 0.220 |
| EBCA (control) | — | 85.28 | 0.158 | −1.55 | 5.19 | | 27.700 | 17.500 |
| EBCA (control) | Cabazitaxel | 103.8 | 0.168 | −1.7 | 6.07 | 3.87 | 0.070 | 0.065 |
| BCA (control) | — | 89.86 | 0.193 | −3.23 | 5.31 | | 23.200 | 19.600 |
| BCA (control) | Cabazitaxel | 92.63 | 0.179 | −4.15 | 6.33 | 3.80 | 0.077 | 0.065 |
| 2-EHCA | Cabazitaxel | 73.01 | 0.453 | −34.3 | 4.43 | 4.28 | 0.052 | 0.074 |
| 1:2 (2-PECA):BCA | Cabazitaxel | 99.12 | 0.20 | −4.26 | 3.73 | 5.41 | 0.043 | 0.069 |
| 1:2 NPCA:BCA | Cabazitaxel | 96.76 | 0.175 | −5.32 | 3.88 | 5.52 | 0.092 | 0.090 |
| 3-HPCA | Cabazitaxel | 76.4 | 0.146 | −2.65 | 4.18 | 4.96 | 0.105 | 0.120 |
| 3-HPCA | Alpelisib | 117.1 | 0.172 | | | | | |
| 3-MBCA | Cabazitaxel | 80.72 | 0.185 | −3.13 | 5.7 | 3.79 | 0.084 | 0.087 |
| 3-MBCA | Alpelisib | 196.4 | 0.196 | | | | | |
| 1-HPCA | Cabazitaxel | 76.53 | 0.247 | −3.26 | 5.58 | 3.83 | 0.040 | 0.065 |
| 2-HPCA | Cabazitaxel | 84.88 | 0.201 | −3.57 | 6.03 | 4.72 | | |
| 1-PCA | Cabazitaxel | 1398 | 0.818 | −3.19 | 5.53 | 4.79 | | |
| 3-PCA | Cabazitaxel | 53.93 | 0.241 | −7.44 | 4.6 | 5.15 | | |
| 3,3-DMBCA | Cabazitaxel | 91.84 | 0.266 | −3.31 | 5.89 | 4.89 | | |

Uses of the New Nanoparticles

According to an embodiment, a composition or solution comprising the new nanoparticles as described herein is provided. The composition or solution may be a pharmaceutical formulation comprising pharmaceutically acceptable excipients and diluents.

An aspect of the invention includes the nanoparticles for use in treatment, as well as a method of treating a disease comprising administering a composition of the invention as defined herein to a subject in need thereof. Exemplary subjects include mammalian subjects such as human subjects.

The present invention also provides the nanoparticles described herein, or a composition or solution comprising the nanoparticles, for use in therapy.

The present invention also provides the nanoparticles described herein, or a composition or solution comprising the nanoparticles, for use in diagnosis.

The present invention also provides the nanoparticles described herein, or a composition or solution comprising the nanoparticles, for use in the treatment of cancer. In this case, the active agent is an anti-cancer agent.

The present invention also provides the nanoparticles described herein, or a composition or solution comprising the nanoparticles, for use in the treatment of an infection. In this case, the active agent is an anti-infection agent.

The present invention also provides the nanoparticles described herein, or a composition or solution comprising the nanoparticles, for use in diagnostic imaging (of the human or animal body). In this case, the active agent is a diagnostic agent.

The present invention also provides a method for the treatment of cancer, the method comprising administering (an effective amount of) the nanoparticles described herein, or a composition or solution comprising the nanoparticles, to a subject in need thereof. In this case, the active agent is an anti-cancer agent. Exemplary subjects include mammals, preferably humans.

The present invention also provides a method for the treatment of an infection, the method comprising administering (an effective amount of) the nanoparticles as defined herein, or a composition comprising the nanoparticles, to a subject in need thereof. In this case, the active agent is an anti-infection agent. Exemplary subjects include mammals, preferably humans.

EXAMPLES

Materials and Methods

Quantification of Alcohol Toxicity

Cell lines: The cell lines were used for determining alcohol cytotoxicity Hep G2 (Human liver cancer cell line), LLC-PK1 (Porcine kidney cell line) and IMR-90 (Human lung fibroblast cell line). All medium was fortified with 10% (w/v) fetal calf serum albumin (Sigma) and 100 units/ml penicillin/streptomycin (PenStrep®, Sigma). All cell lines were obtained from ATCC and were routinely tested for *mycoplasma*. Cells growing in 24- or 96-well plates were incubated with serial dilutions of the alcohol for 24 h, at 37° C. in an atmosphere of 5% $CO_2$. The toxicity was assessed the commonly used MTT (3-(4,5-dimethylthiazol-2-yl)-2,5-diphenyltetrazolium bromide) cell viability assay.

MTT cell viability assay. The cells were incubated for 24 with the different nanoparticles/substances. The cell medium was then aspirated and exchanged with 100 µl of medium containing a final concentration of 250 µg MTT/ml. The incubation was continued for 3 h at 37° C. for formation of the formazan-particles, which were dissolved in DMSO with 1% (v/v) $NH_4Cl$. The absorbance was read in a plate reader (Biosys Ltd, Essex, UK) at 570 nm, and background from absorbance at 650 nm was subtracted.

Solubility of API/Dyes with ACA Monomers

Small quantities (typically 5.0 mg) of chosen API/dye were blended with ACA monomer (typically 100 ul), containing dual action inhibitor if appropriate (typically, 5-10 wt %, vanillin, Sigma Aldrich, Germany), to be tested and monitored for 24 h. Solubility and degree of polymerization were monitored visually.

Synthesis and Characterization of Nanoparticles

PEGylated PACA nanoparticles were synthesized by miniemulsion polymerization. An oil phase consisting of 0.8 g alkylcyanoacrylate or blend of alkylcyanoacrylates (monomer, Cuantum Medical Cosmetics, Spain, or Loctite, Ireland) containing 0-5.0% (w/w) dual inhibiter, typically vanillin (Sigma Aldrich, Germany) and 0-5% (w/w) costabilisor Miglyol 812 (Cremer, USA) was prepared. Fluorescent particles for optical imaging, were prepared by adding NR668 (modified Nile Red)[40], custom synthesis, 0.59% (w/w) to the oil phase. Particles containing active pharmaceutical ingredient were prepared by 0-5% API (w/w) to the oil phase, for example, cabazitaxel(CBz, 5% (w/w), Biochempartner Co. Ltd., China, product item number BCP02404).

An aqueous phase consisting of 0.1 M HCl (12 g) containing Brij L23 (8 mM, Sigma, USA) and Kolliphor HS15 (10.2 mM, Sigma, Germany) was added to the oil phase and immediately sonicated for 3 min on ice (6×30 sec intervals, 50% amplitude, Branson Ultrasonics digital sonifier 450, USA). The solution was rotated (15 rpm, SB3 rotator, Stuart, UK) at room temperature overnight before adjusting the pH to 5 using 1 M NaOH. The polymerization was continued for 5 h at room temperature on rotation. The dispersion was dialyzed (Spectra/Por dialysis membrane MWCO 100,000 Da, Spectrum Labs, USA) against water to remove unreacted PEG. The size, polydispersity index (PDI) and the zeta potential of the nanoparticles were measured by dynamic light scattering and laser Doppler Micro-electrophoresis using a Zetasizer Nano ZS (Malvern Instruments, UK). To calculate the amount of encapsulated drug, the drug was extracted from the particles by dissolving them in acetone (1:10), and quantified by liquid chromatography coupled to mass spectrometry (LC-MS/MS) as described below.

API Quantification by LC/MS, Exemplified by Quantification of CBz

CBZ quantification by LC-MS/MS. CBZ, as the pure chemical or part of nanoparticles, was quantified by LC-MS/MS, using an Agilent 1290 HPLC system coupled to an Agilent 6490 triple quadrupole mass spectrometer. The HPLC column was an Ascentis Express C8, 75×2.1 mm, 2.7 µm particles size with a 5×2.1 mm guard column of the same material (Sigma), run at 40° C. Eluent A was 25 mM formic acid in water and eluent B was 100% methanol, and flow rate was 0.5 ml/min. The mobile phase gradient was isocratic at 55% B for 1.5 min, then from 55% to 80% B over 1 min, followed by 1 min washout time and subsequently column re-equilibration. Injection volume was 5.00 µl. MS detection was in positive ESI mode (Agilent Jetstream) quantified in multiple reaction monitoring (MRM) mode using the transition m/z 858.3→577.2. The parent ion was chosen to be the Na adduct as this gave the best sensitivity. Similarly, the hexadeuterated internal standard was detected on the 864.4→583.2 transition. Both analytes were run at 380 V fragmentor and 20 V collision energy.

Reference standards were used for accurate quantification. The unlabeled CBZ standard was the same as used for synthesis (see above) at >98% purity. Hexadeuterated CBZ internal standard was purchased from Toronto Research Chemicals (Toronto, Canada; catalogue number C046502 at 99.6% isotopic purity). Standards were dissolved in acetone and were used to build an unlabeled standard series spanning at least five concentration points.

The limit of quantification (LOQ) was calculated from six replicate quantifications of the lowest concentration point in the standard curves (0.1 ng/ml), specifically as the average plus six standard deviations; this amounted to an LOQ of 0.19 ng/ml (signal/noise ratio >20). Accuracy based on the same standard sample set was 8.8% and precision was 18.0%.

Quantification of PACA Nanoparticle Toxicity

Cell lines: The cell lines were used for determining alcohol cytotoxicity Hep G2 (Human liver cancer cell line), LLC-PK1 (Porcine kidney cell line) All medium was fortified with 10% (w/v) fetal calf serum albumin (Sigma) and 100 units/ml penicillin/streptomycin (PenStrep®, Sigma). All cell lines were obtained from ATCC and were routinely tested for *mycoplasma*. Cells growing in 24- or 96-well plates were incubated with serial dilutions of the alcohol for 24 h, at 37° C. in an atmosphere of 5% $CO_2$. The toxicity was assessed the commonly used MTT (3-(4,5-dimethylthiazol-2-yl)-2,5-diphenyltetrazolium bromide) cell viability assay and the commonly used LDH assay.

MTT cell viability assay. The cells were incubated for 24 h with the different Nanoparticles. The cell medium was then aspirated and exchanged with 100 μl of medium containing a final concentration of 250 μg MTT/ml. The incubation was continued for 3 h at 37° C. for formation of the formazan-particles, which were dissolved in DMSO with 1% (v/v) $NH_4Cl$. The absorbance was read in a plate reader (Biosys Ltd, Essex, UK) at 570 nm, and background from absorbance at 650 nm was subtracted.

LDH Cytotoxicity assay. Using LDH cytotoxicity assay kit (K311-400, Biovision). The cells were incubated for 24 h with the different nanoparticles and 100 ul of reaction mixture (prepared to manufacture's method) transferred to each well of the plates. The mixture was incubated for 20 min at 37° C.

The absorbance was read in a plate reader (Biosys Ltd, Essex, UK) at 490 nm, and background from absorbance at 680 nm was subtracted.

Quantification of PACA Nanoparticle Efficacy, Exemplified by Use of CBz Loaded Particles Cell lines: The cell lines used for determining particle efficacy were A549 (Humang lung epithelia cells), DU-145 (Human prostate epithelial cells). All medium was fortified with 10% (w/v) fetal calf serum albumin (Sigma) and 100 units/ml penicillin/streptomycin (PenStrep®, Sigma). All cell lines were obtained from ATCC and were routinely tested for *mycoplasma*. Cells growing in 24- or 96-well plates were incubated with serial dilutions of the particles for 24 h, at 37° C. in an atmosphere of 5% $CO_2$. The toxicity was assessed the commonly used ATP measuring CellTiter-Glo® assay.

Cell viability estimated by measuring ATP. Viability of the cells was tested measuring the ATP levels by using the CellTiter-Glo® (Promega, WI, USA) assay, as described by the supplier. Cells were incubated with nanoparticles (empty or containing Cbz) for 48 h, thereafter one half of the volume was removed, replaced with an equal volume of the ATP reagent and gently mixed. After incubation for 10 min the cell lysate was transferred to a light-protected 96-well plate and luminescence measured in a plate reader (Biosys Ltd, Essex, UK).

Preparation of PACA-Np Stabilized Microbubbles

NP-stabilized MBs (also referred to as NPMB) were prepared by self-assembly of the nanoparticles (1 wt %, 10 mg/ml) at the gas-water interface by the addition of 0.5% casein in phosphate-buffered saline and vigorous stirring using an ultra-turrax (T-25, IKAWerke, Staufen, Germany) as described (Mørch, et al. 2015). Perfluoropropane (F2 Chemicals, Preston, Lancashire, UK) was used. The average MB diameter, size distribution and concentration were determined using light microscopy and image analysis (ImageJ 1.48v, National Institute of Health, Bethesda, MA, USA). The NPMB solution is a combination of free nanoparticles and NPMBs, where only a small percentage of the nanoparticles are located on MBs.

Results

The methods and materials discussed above were used to generate the results reported in Tables 2-5.

Alcohol toxicity is disclosed in Table 3: Alcohol toxicity was assessed by exposure of the cells to a given concentration of alcohol to a limit of 3 wt %. Cell activity was determined after 24 h and compared to an untreated control. Data is reported as percentage remaining cell activity (vs control) in 3% alcohol in three individual cell lines. The greater the percentage of remaining activity, the lower the toxicity of the alcohol to the cell line. Thus, Hep G2 cells exposed to 3 wt % 2-ethylhexanol retained 91.2% activity, whereas Hep G2 cells exposed to 3 wt % 2-ethylbutanol retained only 74.6% activity. Thus 2-ethylhexanol is less toxic to Hep G2 cells than 2-ethylbutanol.

Particle toxicity is disclosed in Table 2: Particle toxicity was assessed by exposure of two cell lines to a range of particle concentrations up to 300 μg/ml. Polymer nanoparticles tested contained no API and were prepared by the methods given above with monomer combinations listed in Table 2. Cell activity was determined after 24 h, and plotted against particle concentration. For each particle/cell type combination, the particle concentration at which 50% cell activity remained was determined (IC50, μg/ml). The higher the concentration of particles needed to reduce cell activity to 50% the lower the toxicity of the particles. Thus, polymer particles made from poly(2-ethylhexyl cyanoacrylate) have an IC 50 of 300 μg/ml when tested against Hep G2 cells, which is 10× higher than poly(octyl cyanoacrylate) particles which have an IC 50 of 32 μg/ml when tested against Hep G2 cells. Thus poly-2-ethylhexylcyanoacrylate particles can be used at 10× higher concentration than poly(octyl cyanoacrylate) particles without causing toxicity.

Results from API solubility are disclosed in Table 4: Here, small amounts of API under test a mixed with given ACA monomer, and the outcome determined visually. Where the result is given as 'soluble', the API was soluble in the choose monomer with no visual residue, and there can be used as a combination to prepare API loaded nanoparticles. If the results are given as insoluble or partially, it is an indication that this combination cannot be used to prepared API loaded nanoparticles.

Table 5 discloses the characterization of nanoparticle batch containing the APIs cabazitaxel or alpelisib. This consists of Z-average particle size, associated polydispersity index (PDI), zetapotential, dry weight and measure API loading. The preferred ranges for which have been discussed above. Finally, efficacy of the particles containing cabazitaxel against two cell lines is reported as an IC 50 value in μg/ml. The lower the number the more effective the particles are against the cell line. All particles reported show efficacy at concentrations significantly below the inherent toxicity of the empty particle (200 to 7000×), indicated a wide safety margin for the given nanoparticle formulations.

Other aspects and embodiments of the invention

Embodiment 1. A new nanoparticle comprising copolymeric or homopolymeric compounds according to formula 1;

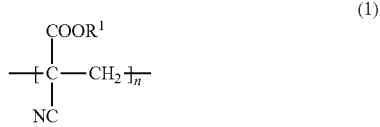

(1)

wherein the compound comprises polymerizable cyanoacrylate monomers according to formula 2:

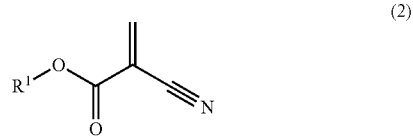

(2)

wherein R1 in at least one of the polymerizable cyanoacrylate monomers is independently selected from the group consisting of 2-ethylhexyl, 2-phenyl ethyl, neopentyl, 1-pentyl, 2-pentyl, 3-pentyl, 3,3-dimethyl-1 butyl, 3-methylbutyl, 1-heptyl, 2-heptyl and 3-heptyl.

Embodiment 2. The nanoparticle according to embodiment 1, wherein R1 in at least one of the polymerizable cyanoacrylate monomers is independently selected from the group consisting of 2-ethylhexyl, 2-phenyl ethyl, neopentyl, 1-pentyl, 2-pentyl, 3-pentyl, 3,3-dimethyl-1 butyl, 1-heptyl, 2-heptyl and 3-heptyl.

Embodiment 3. The nanoparticle according to embodiment 1, wherein R1 in at least one of the polymerizable cyanoacrylate monomers is independently selected from 2-ethylhexyl, 1-heptyl or 2-phenylethyl.

Embodiment 4. The nanoparticle according to anyone of embodiments 1-3, wherein the particle is made from anionic polymerization of a miniemulsion.

Embodiment 5. The nanoparticle according to embodiment 1, wherein the particle is made from anionic polymerization of a miniemulsion and R1 in at least one of the polymerizable cyanoacrylate monomers is 3-methylbutyl.

Embodiment 6. The nanoparticle according to any previous embodiments, comprising an active agent.

Embodiment 7. The nanoparticle according to any previous embodiments, wherein the active agent is selected from the group consisting of alpelisib, a taxane, such as cabazitaxel and docetaxel, a platin, such as oxaliplatin, mupirocin, belinostat, Nile red or NR668.

Embodiment 8. A composition comprising a nanoparticle as defined in any of embodiments 1-7 and optionally one or more pharmaceutically acceptable carriers, diluents or excipients.

Embodiment 9. A nanoparticle according to any of embodiments 1-7 for use in medicine, preferably for use in drug delivery or molecular imaging.

Embodiment 10. Use of a nanoparticle according to any one of embodiments 1-7 in agriculture, aquaculture, antibacterial applications, nutraceuticals, food/feed applications, cosmetics, self-healing, household applications and body care.

The invention claimed is:

1. A nanoparticle comprising copolymeric or homopolymeric compounds which comprise cyanoacrylate subunits according to formula 2A:

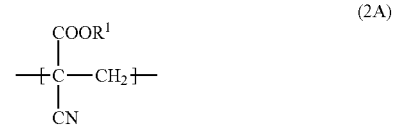

(2A)

wherein each $R^1$ is independently selected from the group consisting of 2-ethylhexyl, 2-phenyl-ethyl, neopentyl, 1-pentyl, 2-pentyl, 3-pentyl, 3,3-dimethyl-1-butyl, 3-methylbutyl, 1-heptyl, 2-heptyl, and 3-heptyl;

and wherein the nanoparticle further comprises an active agent.

2. The nanoparticle of claim 1, wherein the active agent is an anti-cancer agent, an anti-infection agent, a central nervous system agent, or a diagnostic or imaging agent.

3. The nanoparticle of claim 2, wherein the active agent is a taxane, a platin, a histone deacetylase inhibitor, a phosphoinositide 3-kinase inhibitor, an antibacterial agent, or a lipophilic stain.

4. The nanoparticle of claim 1, wherein each $R^1$ is independently selected from the group consisting of 2-ethylhexyl, 2-phenyl-ethyl, neopentyl, 1-pentyl, 3-pentyl, 3,3-dimethyl-1-butyl, 3-methylbutyl, 1-heptyl, 2-heptyl, and 3-heptyl.

5. The nanoparticle of claim 1, wherein each $R^1$ is independently selected from the group consisting of 2-ethylhexyl, neopentyl, 1-pentyl, 2-pentyl, 3-pentyl, 3,3-dimethyl-1-butyl, 3-methylbutyl, 1-heptyl, 2-heptyl, and 3-heptyl.

6. The nanoparticle of claim 1, wherein the nanoparticle comprises copolymeric compounds which comprise (i) cyanoacrylate subunits according to formula 2A; and (ii) cyanoacrylate subunits according to formula 2B

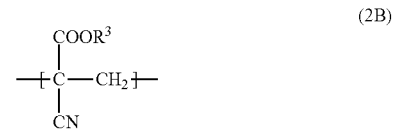

(2B)

wherein each $R^3$ is independently selected from a group having from 1 to 15 non-hydrogen atoms, provided that $R^3$ is not 2-ethylhexyl, 2-phenyl-ethyl, neopentyl, 1-pentyl, 2-pentyl, 3-pentyl, 3,3-dimethyl-1-butyl, 3-methylbutyl, 1-heptyl, 2-heptyl, or 3-heptyl.

7. The nanoparticle of claim 1, wherein the nanoparticle comprises copolymeric or homopolymeric compounds which comprise cyanoacrylate subunits according to formula 2A wherein $R^1$ is 2-phenyl-ethyl.

8. The nanoparticle of claim 7, wherein the nanoparticle comprises copolymeric compounds which comprise (i) cyanoacrylate subunits according to formula 2A wherein $R^1$ is 2-phenyl-ethyl; and (ii) cyanoacrylate subunits according to formula 2B:

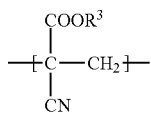

(2B)

wherein each $R^3$ is independently selected from a group having from 1 to 15 non-hydrogen atoms, provided that $R^3$ is not 2-ethylhexyl, 2-phenyl-ethyl, neopentyl, 1-pentyl, 2-pentyl, 3-pentyl, 3,3-dimethyl-1-butyl, 3-methylbutyl, 1-heptyl, 2-heptyl, or 3-heptyl.

9. The nanoparticle of claim 7, wherein the nanoparticle comprises copolymeric compounds which comprise (i) cyanoacrylate subunits according to formula 2A wherein $R^1$ is 2-phenyl-ethyl; and (ii) cyanoacrylate subunits according to formula 2A wherein each $R^1$ is independently selected from the group consisting of 2-ethylhexyl, neopentyl, 1-pentyl, 2-pentyl, 3-pentyl, 3,3-dimethyl-1-butyl, 3-methylbutyl, 1-heptyl, 2-heptyl, and 3-heptyl.

10. The nanoparticle of claim 1, wherein each $R^1$ is independently selected from the group consisting of 2-ethylhexyl, neopentyl, 3-methylbutyl, 1-heptyl, and 3-heptyl.

11. The nanoparticle of claim 10, wherein each $R^1$ is independently selected from the group consisting of 2-ethylhexyl, and 1-heptyl.

12. The nanoparticle of claim 10, wherein $R^1$ is 2-ethylhexyl.

13. The nanoparticle of claim 1, wherein each $R^1$ is independently selected from the group consisting of 2-ethylhexyl, 1-pentyl, 3-pentyl, 3,3-dimethyl-1-butyl, 3-methylbutyl, 1-heptyl, 2-heptyl, and 3-heptyl.

14. The nanoparticle of claim 13, wherein each $R^1$ is independently selected from the group consisting of 3-pentyl, 3,3-dimethyl-1-butyl, and 3-heptyl.

15. The nanoparticle of claim 13, wherein each $R^1$ is independently selected from the group consisting of 2-ethylhexyl, 3-pentyl, 3,3-dimethyl-1-butyl, and 3-heptyl.

16. The nanoparticle of claim 13, wherein each $R^1$ is independently selected from the group consisting of 3,3-dimethyl-1-butyl, 3-methylbutyl, and 3-heptyl.

17. The nanoparticle of claim 13, wherein each $R^1$ is independently selected from the group consisting of 3,3-dimethyl-1-butyl and 3-heptyl.

18. The nanoparticle according to claim 1, wherein the particle is made from the anionic or radical polymerization of a miniemulsion.

19. A method of forming the nanoparticle of claim 1, the method comprising the anionic or radical polymerization of an oil-in-water miniemulsion, wherein said miniemulsion comprises:

(i) cyanoacrylate monomers according to formula 2

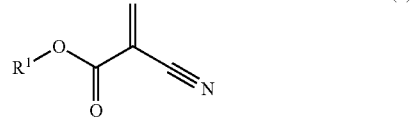

(2)

wherein each $R^1$ is independently selected from the group consisting of 2-ethylhexyl, 2-phenyl-ethyl, neopentyl, 1-pentyl, 2-pentyl, 3-pentyl, 3,3-dimethyl-1-butyl, 3-methylbutyl, 1-heptyl, 2-heptyl, and 3-heptyl;
(ii) at least one surfactant;
(iii) one or more active agents;
(iv) optionally an anionic polymerisation initiator or a radial polymerisation initiator; and
(v) optionally an anionic and/or radical inhibitor.

20. The nanoparticle of claim 1, wherein the active agent is an anti-cancer agent.

* * * * *